United States Patent
Lim (10) Patent No.: US 9,683,956 B2
(45) Date of Patent: Jun. 20, 2017

(54) METHOD OF MANUFACTURING NANO GAP SENSOR USING RESIDUAL STRESS AND NANO GAP SENSOR MANUFACTURED THEREBY

(71) Applicant: KOOKMIN UNIVERSITY INDUSTRY ACADEMY COOPERATION FOUNDATION, Seongbuk-gu, Seoul (KR)

(72) Inventor: Sihyung Lim, Seoul (KR)

(73) Assignee: Kookmin University Industry Academy Cooperation Foundation, Seoul (KR)

(*) Notice: Subject to any disclaimer, the term of this patent is extended or adjusted under 35 U.S.C. 154(b) by 0 days.

(21) Appl. No.: 15/114,782

(22) PCT Filed: Jun. 25, 2015

(86) PCT No.: PCT/KR2015/006468
§ 371 (c)(1),
(2) Date: Jul. 27, 2016

(87) PCT Pub. No.: WO2015/199455
PCT Pub. Date: Dec. 30, 2015

(65) Prior Publication Data
US 2016/0341688 A1  Nov. 24, 2016

(30) Foreign Application Priority Data
Jun. 26, 2014  (KR) .................. 10-2014-0078877

(51) Int. Cl.
*G01N 27/403* (2006.01)
*C23C 14/18* (2006.01)
(Continued)

(52) U.S. Cl.
CPC .......... *G01N 27/403* (2013.01); *C23C 14/18* (2013.01); *C23C 14/185* (2013.01); *C23C 14/34* (2013.01);
(Continued)

(58) Field of Classification Search
None
See application file for complete search history.

(56) References Cited

U.S. PATENT DOCUMENTS 7,056,446 B2 * 6/2006 Nagase ................ G01N 27/07
204/192.1
9,068,914 B2 6/2015 Shim et al.
(Continued)

FOREIGN PATENT DOCUMENTS

KR 10-2013-0113206 10/2013

OTHER PUBLICATIONS

Jang, B. et al. Nanogap-based electrical hydrogen sensors fabricated from Pd-PMMA hybrid thin films. Sensors and Actuators B: Chemical, Mar. 31, 2014, vol. 193, pp. 530-535.
(Continued)

*Primary Examiner* — Shamim Ahmed
(74) *Attorney, Agent, or Firm* — McCarter & English, LLP (57) ABSTRACT

Provided are a method of manufacturing a nano gap sensor and a nano gap sensor manufactured by the method. According to the method of manufacturing the nano gap sensor, fine cracks are formed in a substrate including a silicon wafer, etc. in order to form the nano gap with simplified processes and low manufacturing costs, and after that, a metal catalyst layer is stacked on the nano gap to manufacture a sensor capable of selectively detecting a certain material or a gas such as hydrogen. In particular, when palladium or a palladium alloy is used as the metal catalyst layer, highly sensitive hydrogen sensors capable of responding various concentrations of hydrogen may be produced in large quantities.

9 Claims, 5 Drawing Sheets

(51) Int. Cl.
    H01B 13/00      (2006.01)
    B44C 1/22       (2006.01)
    G01N 33/50      (2006.01)
    H01L 21/3065    (2006.01)
    C23C 14/34      (2006.01)
    G01N 33/487     (2006.01)

(52) U.S. Cl.
    CPC ....... G01N 33/48721 (2013.01); G01N 33/50 (2013.01); H01L 21/3065 (2013.01)

(56) References Cited

U.S. PATENT DOCUMENTS

| | | | |
|---|---|---|---|
| 2010/0112493 A1 | 5/2010 | Adelung et al. | |
| 2013/0186757 A1* | 7/2013 | Reinhart | C12Q 1/6869 204/452 |
| 2014/0113356 A1* | 4/2014 | Tseng | G01N 33/48721 435/283.1 |
| 2015/0027980 A1* | 1/2015 | Van Der Zaag | G01N 33/48721 216/17 |
| 2016/0245789 A1* | 8/2016 | Ikeda | G01N 33/48721 |

OTHER PUBLICATIONS

Lee, J. et al., Highly Mobile Palladium thin Films on an Elastomeric Substrate: Nanogap-Based Hydrogen Gas Sensors. Angewandte Chemie International Edition, 2011, vol. 50, pp. 5301-5305.

Bhatnagar, K. et al., Fluorescence enhancement from nano-gap embedded plasmonic gratings by a navel fabrication technique with HD-DVD. Nanotechnology, 2012, vol. 23, 595201.

International Search Report and Written Opinion mailed Jan. 27, 2016 in corresponding International Appication No. PCT/KR2015/006468.

* cited by examiner

FIG. 3

METHOD OF MANUFACTURING NANO GAP SENSOR USING RESIDUAL STRESS AND NANO GAP SENSOR MANUFACTURED THEREBY

CROSS-REFERENCE TO RELATED APPLICATIONS

This application is the National Stage entry under 35 U.S.C. §371 of International Application No. PCT/KR2015/006468 filed on Jun. 25, 2015, published on Dec. 30, 2015 under publication number WO 2015/199455 A2, which claims the benefit of priority under 35 U.S.C. §119 of Korean Patent Application Number 10-2014-0078877 filed Jun. 26, 2014.

TECHNICAL FIELD

The inventive concept relates to a method of manufacturing a nano gap sensor and a nano gap sensor manufactured by the method, and more particularly, to a method of manufacturing a nano gap sensor using a residual stress of a thin film formed on a base material and a nano gap sensor manufactured by the method.

BACKGROUND ART

In general, a nano gap is an electrode in which metal structures have a gap of tens of nanometers to hundreds of nanometers and may be used in researches on the electrical properties of a nano-sized structure or as a sensor for sensing a chemical material or a biological material in an ultra-fine amount. In particular, a nano gap is essential in measuring a variation of electrical properties at a molecular level.

A conventional technology for manufacturing a nano gap may include a method of generating a gap at a certain location of a metal wire by using electromigration (Appl. Phys. Lett 75, 301), a method of using an electron-beam lithography (Appl. Phys. Lett 80, 865), and a method of depositing metal thin films by using soft substrates (KR2013-0125183).

However, the method of manufacturing the nano gap via electromigration is based on a principle in which an electric current flows in a metal wire having a line width of about hundreds of nanometers or less and atoms in the metal wire collides with electrons and migrate to generate nano gaps. Therefore, it is difficult to control a size of the nano gap and a location where the nano gap is formed.

In the method of manufacturing the nano gap via electron-beam lithography, a size of the nano gap and a location where the nano gap is formed may be accurately controlled since a pattern is directly drawn by an electron beam. However, manufacturing a nano gap by this method is expensive.

According to the method of manufacturing the nano gap on a flexible substrate via a tensile strain, a size or a location of the nano gap cannot be controlled, productivity degrades, and nano gaps having uniform performance and characteristics may not be obtained.

On the contrary, a method in which a spacer is located at a side of a first electrode and a second electrode is formed, and then, the spacer is removed to form a nano gap electrode has been suggested. However, manufacturing processes are complicated and it is difficult to adjust a width of a nano gap, and moreover, a plurality of nano gap electrode devices may not be manufactured at a time.

In addition, an electrochemical deposition method may be used, that is, metal electrode patterns spaced apart by a relatively large gap are formed on a certain substrate, an electric power is supplied to the metal electrode patterns with the substrate entirely immersed into a certain electrolyte so that an electrode material layer is deposited on a surface of the metal electrode patterns and is grown to reduce a width of the gap and generate a nano gap. However, the manufacturing processes are complicated and it is difficult to adjust a size of the nano gap.

In addition, according to a method of manufacturing nano gap by using a shadow mask, in which a nanostructure such as a nanotube is placed and a metal material is deposited so as to generate a nano gap as large as a size of the nanostructure, a size of the manufactured nano gap is dependent upon a size of the nanostructure and it is difficult to form the nano gap at a desired location.

As described above, the nano gaps manufactured by the prior art may not have uniform quality, and thus, when a nano gap is used as a sensor for detecting a target material or gas, a large error between a magnitude of a response signal and a signal range may occur. Thus, the nano gap used as a sensor may not have uniform performance and may have low reliability, and accordingly, it is difficult to mass produce and commercialize nano gaps formed using these methods.

DETAILED DESCRIPTION OF THE INVENTIVE CONCEPT

Technical Problem

The inventive concept provides a method of manufacturing a nano gap sensor, whereby nano gap sensors having a simplified structure and excellent quality may be mass produced, and a nano gap sensor manufactured by the method.

Technical Solution

According to an aspect of the inventive concept, there is provided a method of manufacturing a nano gap sensor, the method including: (a) forming one or more concave portions having notch shapes at an edge of a surface of a substrate; (b) forming an insulating layer on the surface of the substrate on which the one or more concave portions are formed so that a crack, which occurs when a residual stress generated between the substrate and the insulating layer concentrates at a sharp end of the one or more concave portions, propagates and forms a nano gap crossing over the surface of the substrate and having a depth corresponding to an entire thickness of the one or more concave portions and the insulating layer; (c) forming one or more sensing patterns on the insulating layer, wherein the one or more sensing patterns cross over the nano gap; and (d) forming electrodes at opposite ends of the one or more sensing patterns.

According to an aspect of the inventive concept, there is provided a nano gap sensor manufactured by the method.

According to an aspect of the inventive concept, there is provided a method of manufacturing a nano gap hydrogen sensor, the method including: (a) forming one or more concave portions having notch shapes at an edge of a surface of a substrate; (b) forming an insulating layer on the surface of the substrate on which the one or more concave portions are formed, so that a crack, which occurs when a residual stress generated between the substrate and the insulating layer concentrates at a sharp end of the one or more concave portions, propagates and forms a nano gap crossing over the surface of the substrate and having a depth corresponding to an entire thickness of the one or more concave portions and the insulating layer; (c) forming one or more sensing patterns on the insulating layer, wherein the one or more sensing patterns comprise palladium (Pd) or a Pd alloy and cross over the nano gap; and (d) forming electrodes at opposite ends of the one or more sensing patterns.

According to an aspect of the inventive concept, there is provided a nano gap hydrogen sensor manufactured by the method.

Advantageous Effects

According to the method of manufacturing a nano gap sensor of one or more exemplary embodiments, a method of forming fine cracks in a substrate including a silicon wafer, etc. is used to manufacture a nano gap with simplified processes and low manufacturing costs, and then, a metal catalyst layer is formed on the nano gap to manufacture a sensor capable of selectively detecting a certain material or a gas such as hydrogen. In particular, when palladium or a palladium alloy is used as the metal catalyst layer, highly sensitive hydrogen sensors capable of responding various concentrations of hydrogen may be produced in large quantities.

BEST MODE

The inventive concept will now be described more fully with reference to the accompanying drawings, in which exemplary embodiments of the inventive concept are shown.

Also, in the description, certain detailed explanations of the related art are omitted when it is deemed that they may unnecessarily obscure the essence of the inventive concept.

As the inventive concept allows for various changes and numerous embodiments, particular embodiments will be illustrated in the drawings and described in detail in the written description. However, this is not intended to limit the inventive concept to particular modes of practice, and it is to be appreciated that all changes, equivalents, and substitutes that do not depart from the spirit and technical scope are encompassed in the inventive concept.

The terms used in the present specification are merely used to describe particular embodiments, and are not intended to limit the inventive concept.

An expression used in the singular encompasses the expression of the plural, unless it has a clearly different meaning in the context. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Figure 1:
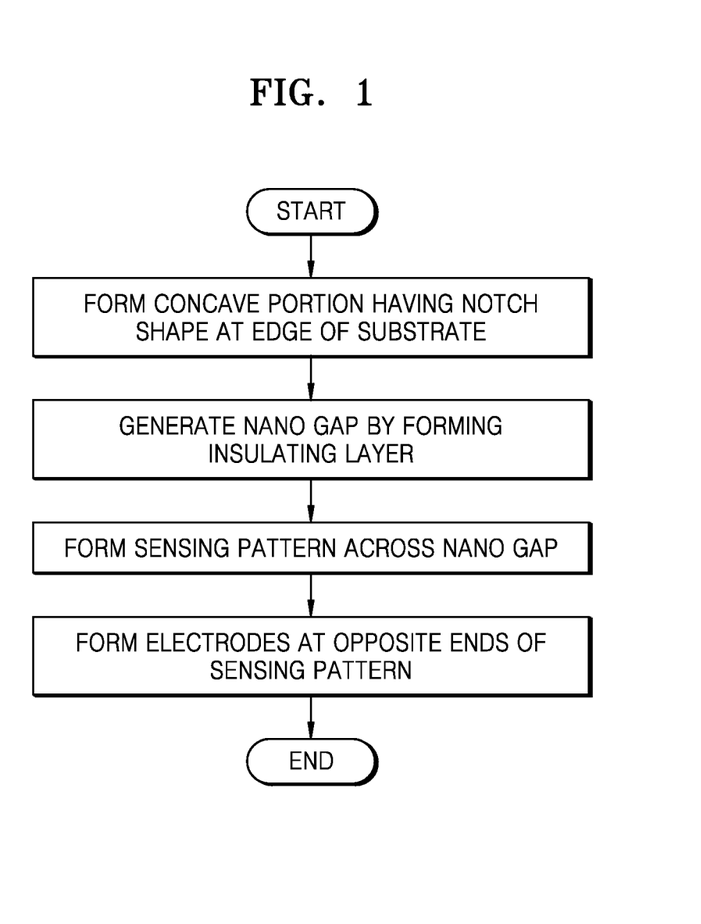
FIG. 1 is a flowchart illustrating a method of manufacturing a nano gap sensor according to an exemplary embodiment.

As shown in FIG. 1, a method of manufacturing a nano gap sensor according to an exemplary embodiment includes: (a) forming one or more concave portions formed as notches at a side on a surface of a substrate; (b) forming an insulating layer on the surface of the substrate, in which the concave portions are formed, to generate a nano gap; (c) forming one or more sensing patterns crossing the nano gap on the insulating layer; and (d) forming electrodes at opposite ends of the sensing patterns, and each of the processes will be described below in detail.

FIGS. 2A to 2G are diagrams illustrating processes of manufacturing the nano gap sensor according to the exemplary embodiment, and hereinafter, the manufacturing processes will be described with reference to the above drawings.

The process (a) of the method of manufacturing the nano gap sensor according to the exemplary embodiment is a process for forming one or more concave portions having notch shapes at a side on a surface of a substrate (11).

Figure 2A:
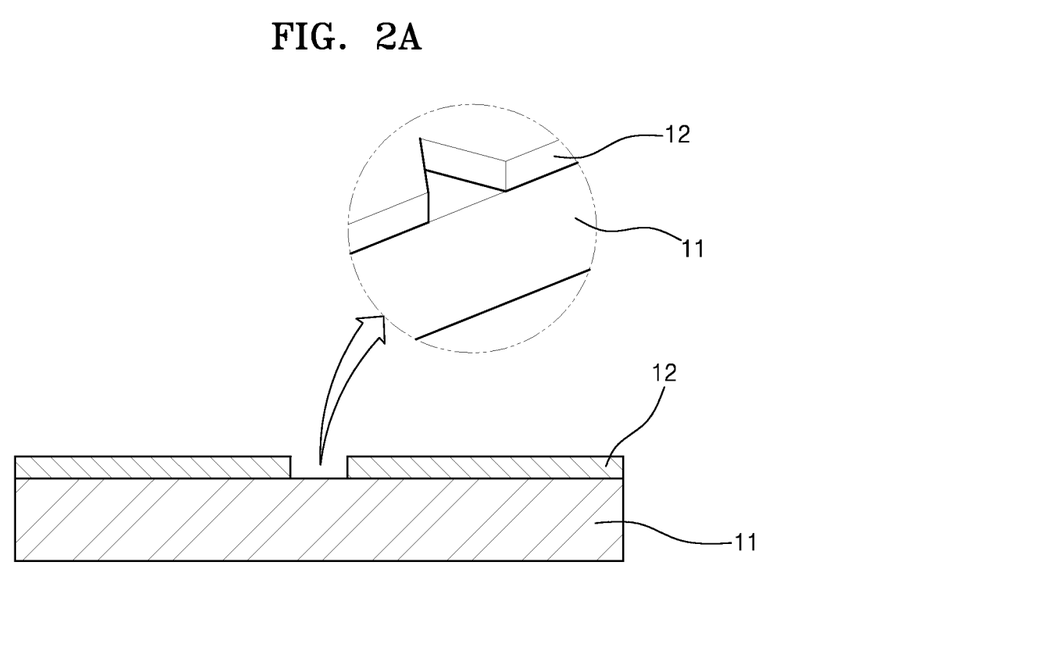
FIGS. 2A to 2G are diagrams illustrating processes of manufacturing the nano gap sensor according to an exemplary embodiment.

Referring to FIG. 2A, a photoresist (PR) solution is applied to an entire surface of the substrate, and a mask having patterns for forming the concave portions of notch shape is fixed on the substrate and exposed to ultraviolet (UV) rays, and then, a exposed portion is developed to form a PR pattern 12 according to a photolithography process.

Here, the substrate 11 may include a single-crystalline or a poly-crystalline inorganic material such as silicon or sapphire.

Figure 2B:
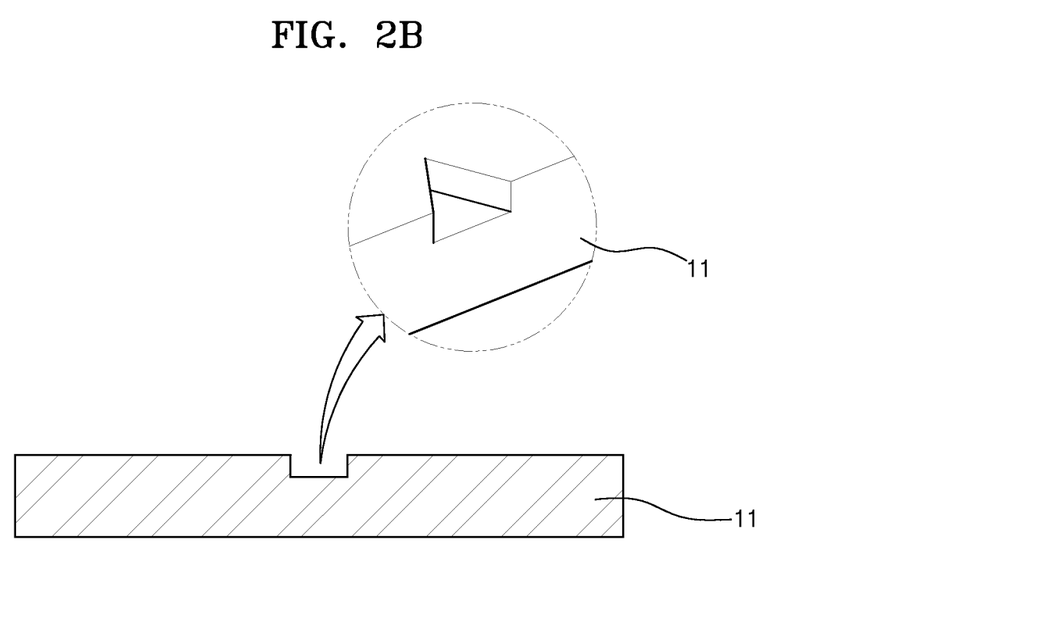
Figure 2C:
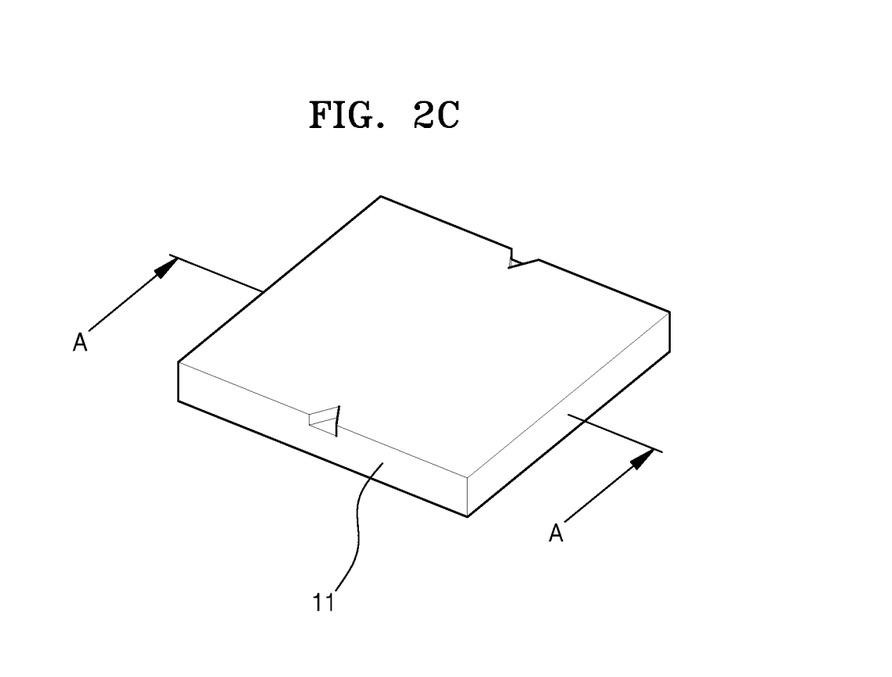

Next, an etching process is performed by using the PR pattern 12 formed on the substrate 11 as a mask in order to form the concave portion having the notch shape, and then, the PR pattern is removed. Then, the substrate having one or more concave portions formed as notches at an edge of the surface of the substrate may be obtained as shown in FIGS. 2B and 2C.

In addition, examples of the etching process for forming the concave portion may include a dry etching process such as a reactive ion etching (RIE), magnetically enhanced RIE (MERIE), inductively coupled plasma (ICP) etching, transformer coupled plasma (TCP) etching, and electron cyclotron resonance (ECR) etching.

Next, the process (b) in the method of manufacturing the nano gap sensor according to the exemplary embodiment is a process of forming an insulating layer on the surface of the substrate, in which the concave portions are formed, to generate a nano gap.

In the present process, an insulating layer including an insulating material such as $Si_3N_4$, $SiO_2$, etc. is formed on the entire surface of the substrate, in which the concave portions are formed, by a chemical vapour deposition method such as a low pressure chemical vapour deposition (LPCVD) method, a plasma-enhanced chemical vapour deposition (PECVD) method, etc. In addition, during formation of the insulating layer, a nano gap crossing over the surface of the substrate is generated due to a crack initiating from a sharp end of the concave portion having the notch shape.

In more detail, in the present process, a residual stress generating between the substrate and the insulating layer during the formation of the insulating layer is concentrated on the sharp end of the concave portion having the notch shape, thereby initiating a crack. In addition, the crack propagates through the substrate so as to form a channelling fracture that crosses over the substrate, and accordingly, the nano gap is formed.

Figure 2D:
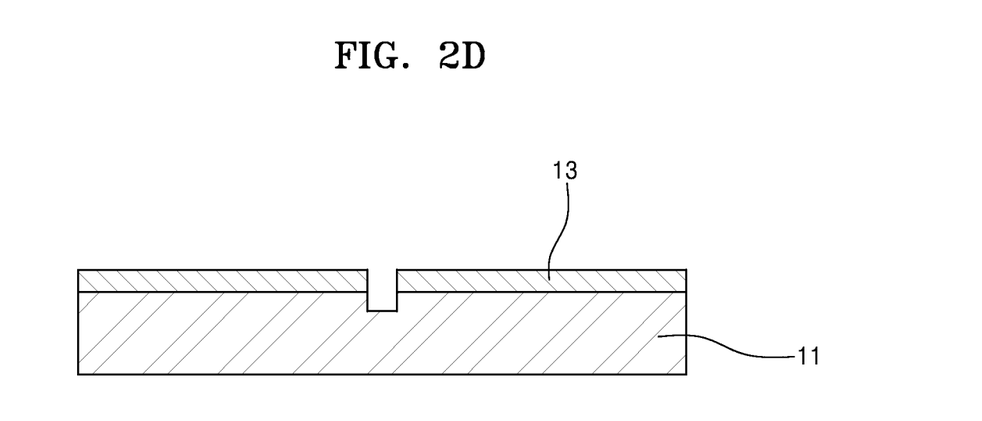

Then, as shown in FIG. 2D showing a cross-section taken along a line A-A' (see FIG. 2C) after performing the above process, a nano gap having a width of about 20 nm to about 70 nm and a depth corresponding to a thickness of the concave portion in the substrate 11 and a thickness of the insulating layer 13 may be formed.

The process (c) in the method of manufacturing the nano gap sensor according to the exemplary embodiment is a process for forming one or more sensing patterns crossing over the nano gap on the insulating layer, for example, the sensing patterns may be formed on the insulating layer by using a lift-off process.

Figure 2E:
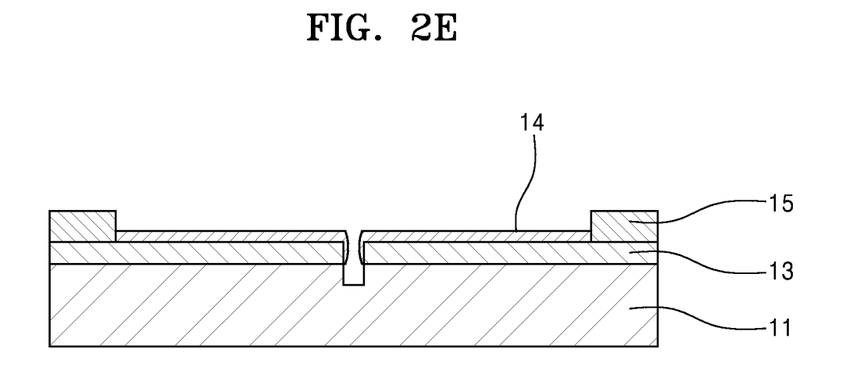

Referring to FIG. 2E, a PR solution is applied on an entire surface of the insulating layer according to a photolithography process, a mask for forming the sensing patterns is fixed on the insulating layer and exposed to UV rays. Then, a developed portion is removed to form a PR pattern 15, and then, a sensing pattern 14 crossing over the nano gap is formed on the insulating layer by a well known deposition method and the PR pattern 15 is removed.

Here, the metal material forming the sensing pattern (14) may include any kind of metal, provided that the metal adsorbs or reacts with a detection target material such as a gas or a biological material and generates a variation in an electric resistance value, for example, Pd, Ni, Pt, Au, Ag and so forth. In particular, if the sensing pattern (14) is a sensing pattern for detecting hydrogen gas, the sensing pattern (14) may include Pd or a Pd alloy. Examples of the Pd alloy may include Pd—Ni, Pd—Pt, Pd—Ag, Pd—Ti, Pd—Fe, Pd—Zn, Pd—Co, Pd—Mn, Pd—Au, Pd—W, etc.

In addition, the sensing pattern (14) may be formed by any deposition method that is generally used in the art, for example, a physical vapour deposition (PVD) method such as an e-beam evaporation method and a sputtering method, and a chemical deposition method such as the CVD method and an atomic layer deposition (ALD) method.

Finally, the process (d) in the method of manufacturing the nano gap sensor according to the exemplary embodiment is a process of forming electrodes at opposite ends of the sensing pattern (14), for example, forming the electrodes on the insulating layer at the opposite ends of the sensing pattern (14) by using a lift-off process.

Figure 2F:
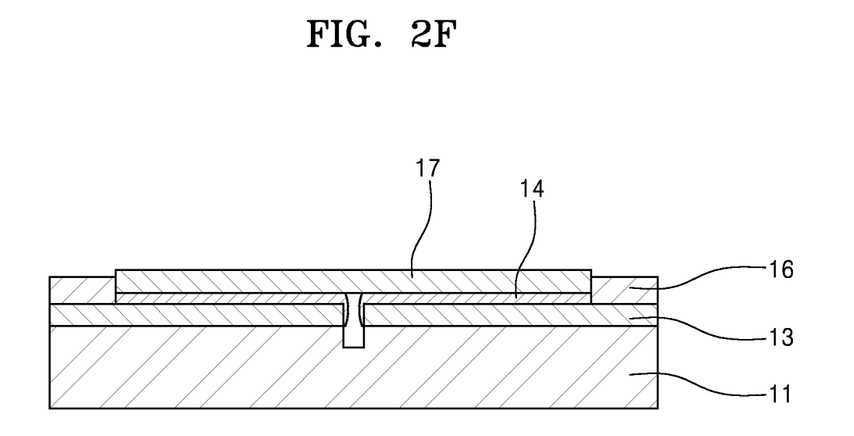
Figure 2G:
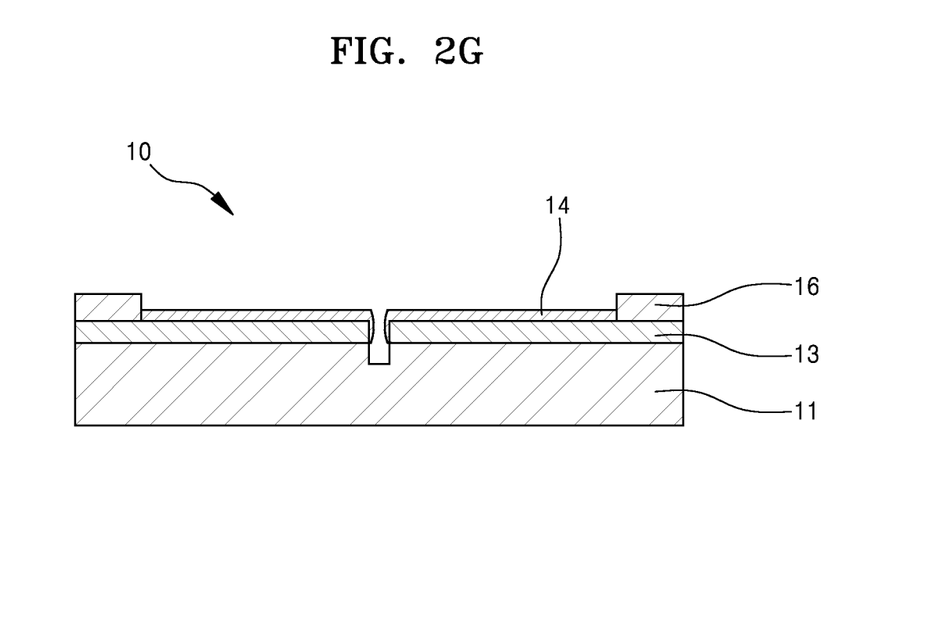

Referring to FIGS. 2F and 2G, a PR solution is applied and a mask for forming the electrodes is fixed thereon and is exposed to the UV rays. Then, a exposed portion is developed to form a PR pattern 17, and electrodes 16 are formed on the opposite ends of the sensing pattern 14 by a well known deposition method. After that, the PR pattern 17 is removed to form a nano gap sensor 10.

In addition, a metal forming the electrodes may have a high electric conductivity, for example, Ti/Au, Ag, Pt, Ni, Cu, etc., and the deposition method for forming the electrodes in the present process may be any method that is generally used in the art. Examples of the deposition method may include a PVD method such as an e-beam evaporation method and a sputtering method, and a chemical deposition method such as the CVD method and an ALD method.

According to the method of manufacturing the nano gap sensor according to the exemplary embodiment as described above, fine fractures are generated in the substrate including a silicon wafer, etc. in order to form the nano gap by using a simplified process, and then, a metal catalyst layer is formed on the nano gap to manufacture a sensor capable of selectively detecting a certain material or a gas such as hydrogen. In particular, if Pd or a Pd alloy is used as the metal catalyst layer, highly sensitive hydrogen sensors responding to various hydrogen concentrations may be produced in large quantities.

The nano gap sensor manufactured as above according to the exemplary embodiment has a voltage-current characteristic, and may sense a variation in the current according to a concentration of an electrical, a chemical, an electrochemical, and a biological analysis target object, or may sense a detectable variation in the voltage-current characteristic thereof caused by a coupling phenomenon occurring between the analysis target object of nanometer scale and a specific complex.

Figure 3:
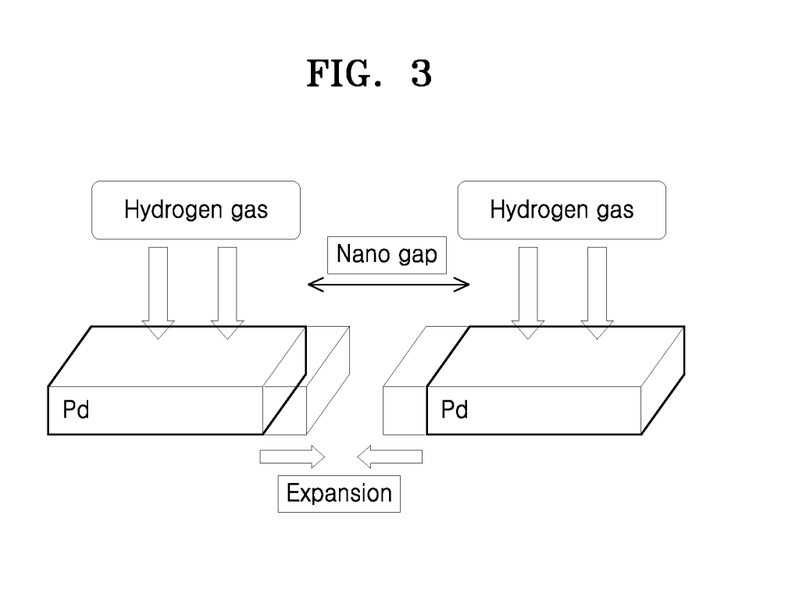
FIG. 3 is a diagram showing an example of a nano gap sensor manufactured by the manufacturing method according to the exemplary embodiment and illustrating a sensing principle of a palladium nano gap hydrogen sensor.

FIG. 3 is a schematic diagram showing an operating principle of a hydrogen sensor when the nano gap sensor is used to detect hydrogen gas. According to the present exemplary embodiment, when hydrogen is introduced in the nano gap sensor having the sensing pattern including Pd, a Pd lattice expands to be formed as a connecting wire, and an electric resistance thereby reduces. Then, the hydrogen gas may be detected.

That is, when the hydrogen gas does not exist, the electric current may not sufficiently flow due to the nano gap, and thus, a high resistance value is shown. However, under the hydrogen atmosphere, a lattice constant of the thin film of the sensing pattern increases to absorb peripheral hydrogen, and an increase in a volume of the thin film results in filling the nano gap so that the electric current sufficiently flows, and thus, a low resistance value is shown. Accordingly, a variation in the resistance value according to the existence of the hydrogen gas is measured to measure a concentration of hydrogen.

Otherwise, the nano gap sensor according to the exemplary embodiment may be used as a bio sensor for detecting a molecular property of a biological sample or existence of the biological sample by placing the biological sample such as a molecule, cells, or antigen-antibody of a nanometer scale in the nano gap.

The analysis target object of the nanometer scale may denote, for example, cells, deoxyribonucleic acid (DNA), protein, antigen-antibody, enzyme-substrate, etc. According to an object to be analyzed, the nano gap sensor may be variously modified. For example, when a DNA molecule is to be analyzed, DNA having opposite ends of thiol groups is fixed on an electrode, and then, gold particles or the like, to which the DNA to be analyzed can be attached, may be fixed thereon. In addition, when protein is to be analyzed, the electrode may be plated with glass, polymer, ceramic, or the like, and an appropriate linker such as cysteine is attached to an exposed part of the electrode so that the protein to be analyzed may be attached to the linker. Also, when an antigen-antibody reaction is to be analyzed, a certain antibody is coupled to a linker as above, and then, a specific antigen may be coupled to the antibody.

EXPLANATIONS OF MAJOR REFERENCE NUMERALS

10: nano gap sensor
11: substrate
12, 15, 17: photoresist pattern
13: insulating layer
14: sensing pattern
16: electrode

The invention claimed is:

1. A method of manufacturing a nano gap sensor, the method comprising:
   (a) forming one or more concave portions having notch shapes at an edge of a surface of a substrate;
   (b) forming an insulating layer on the surface of the substrate on which the one or more concave portions are formed so that a crack, which occurs when a residual stress generated between the substrate and the insulating layer concentrates at a sharp end of the one or more concave portions, propagates and forms a nano gap crossing over the surface of the substrate and having a depth corresponding to an entire thickness of the one or more concave portions and the insulating layer;
   (c) forming one or more sensing patterns on the insulating layer, wherein the one or more sensing patterns cross over the nano gap; and
   (d) forming electrodes at opposite ends of the one or more sensing patterns.

2. The method of claim 1, wherein the substrate comprises a silicon wafer.

3. The method of claim 1, wherein in (a), the one or more concave portions are formed by dry etching.

4. The method of claim 1, wherein in (b), the insulating layer comprises silicon nitride ($Si_3N_4$).

5. The method of claim 1, wherein the nano gap has a width of about 20 nm to about 70 nm.

6. A method of manufacturing a nano gap hydrogen sensor, the method comprising:
   (a) forming one or more concave portions having notch shapes at an edge of a surface of a substrate;
   (b) forming an insulating layer on the surface of the substrate on which the one or more concave portions are formed, so that a crack, which occurs when a residual stress generated between the substrate and the insulating layer concentrates at a sharp end of the one or more concave portions, propagates and forms a nano gap crossing over the surface of the substrate and having a depth corresponding to an entire thickness of the one or more concave portions and the insulating layer;
   (c) forming one or more sensing patterns on the insulating layer, wherein the one or more sensing patterns comprise palladium (Pd) or a Pd alloy and cross over the nano gap; and
   (d) forming electrodes at opposite ends of the one or more sensing patterns.

7. The method of claim 6, wherein the Pd alloy is one selected from the group consisting of Pd—Ni, Pd—Pt, Pd—Ag, Pd—Ti, Pd—Fe, Pd—Zn, Pd—Co, Pd—Mn, Pd—Au, and Pd—W.

8. A nano gap sensor manufactured by the method according to claim 1.

9. A nano gap hydrogen sensor manufactured by the method according to claim 6.

* * * * *